(12) United States Patent
McKenna et al.

(10) Patent No.: US 8,251,994 B2
(45) Date of Patent: Aug. 28, 2012

(54) VESSEL SEALER AND DIVIDER WITH BLADE DEPLOYMENT ALARM

(75) Inventors: Nicole McKenna, Boulder, CO (US); Geneva Wilkesanders, Superior, CO (US); J. Bruce Dunne, Longmont, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 726 days.

(21) Appl. No.: 12/419,729

(22) Filed: Apr. 7, 2009

(65) Prior Publication Data

US 2010/0256635 A1    Oct. 7, 2010

(51) Int. Cl.
*A61B 18/18* (2006.01)
*A61B 17/00* (2006.01)
*A61B 18/04* (2006.01)

(52) U.S. Cl. ............... 606/41; 606/1; 606/32; 606/205; 606/207

(58) Field of Classification Search .............. 606/32–52, 606/205–207
See application file for complete search history.

(56) References Cited

U.S. PATENT DOCUMENTS

| | | | |
|---|---|---|---|
| 3,923,063 A | 12/1975 | Andrews et al. | |
| 4,102,341 A | 7/1978 | Ikuno et al. | |
| 4,188,927 A | 2/1980 | Harris | |
| 4,200,105 A * | 4/1980 | Gonser | 606/35 |
| 4,535,773 A * | 8/1985 | Yoon | 606/185 |
| 4,800,878 A | 1/1989 | Cartmell | |
| 5,817,091 A | 10/1998 | Nardella et al. | |
| 6,039,732 A | 3/2000 | Ichikawa et al. | |
| 6,849,073 B2 | 2/2005 | Hoey et al. | |
| 7,220,260 B2 | 5/2007 | Fleming et al. | |
| 2007/0043352 A1 * | 2/2007 | Garrison et al. | 606/51 |
| 2007/0142832 A1 * | 6/2007 | Sartor et al. | 606/45 |
| 2008/0200912 A1 * | 8/2008 | Long | 606/37 |
| 2008/0300580 A1 * | 12/2008 | Shelton et al. | 606/1 |
| 2008/0319292 A1 * | 12/2008 | Say et al. | 600/347 |
| 2009/0204137 A1 * | 8/2009 | Maxwell | 606/172 |
| 2009/0326531 A1 * | 12/2009 | Geiselhart | 606/52 |

FOREIGN PATENT DOCUMENTS

| | | |
|---|---|---|
| CA | 2104423 | 2/1994 |
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |

(Continued)

OTHER PUBLICATIONS

International Search Report EP 10159205 dated Jul. 7, 2010.

(Continued)

*Primary Examiner* — Linda Dvorak
*Assistant Examiner* — Brian M Antiskay

(57) ABSTRACT

An electrosurgical forceps includes a selectively advanceable knife and a knife deployment alarm configured to emit a signal under predetermined conditions. An alarm is configured to emit a signal when the cutting blade moves relative to the blade channel. A series of resistances are arranged so that a shorting of each resistor is indicative of a predetermined operating condition triggering the alarm to emit a signal. Pressure sensors, optical measurement devices, and electrical contacts are envisioned for determining blade or trigger actuation or translation.

17 Claims, 11 Drawing Sheets

FOREIGN PATENT DOCUMENTS

| | | |
|---|---|---|
| DE | 19608716 | 4/1997 |
| DE | 19751106 | 5/1998 |
| DE | 19751108 | 5/1999 |
| DE | 19738457 | 1/2009 |
| EP | 1159926 | 12/2001 |
| EP | 1 997 439 A2 | 12/2008 |
| EP | 1997439 | 12/2008 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| RU | 401367 | 11/1974 |
| WO | WO 2008/040483 A1 | 4/2008 |
| WO | WO2008040483 | 4/2008 |

OTHER PUBLICATIONS

European Search Report corresponding to European Application No. EP 10 15 9205.3, completed Jun. 22, 2010; mailed Jul. 7, 2010; 6 pages.
U.S. Appl. No. 12/336,970, filed Dec. 17, 2008.
U.S. Appl. No. 12/399,614, filed Mar. 6, 2009.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/233,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/244,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Sep. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331.643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Venous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

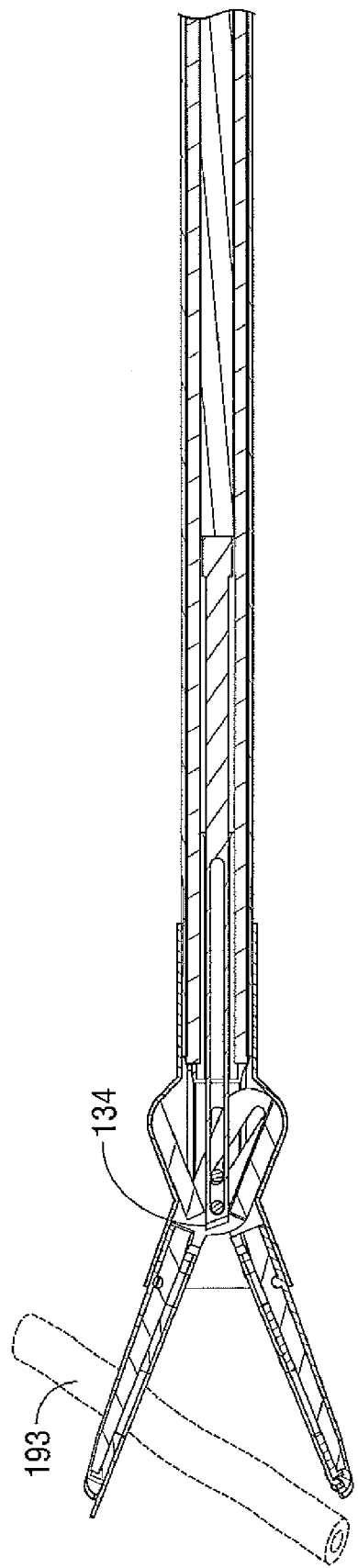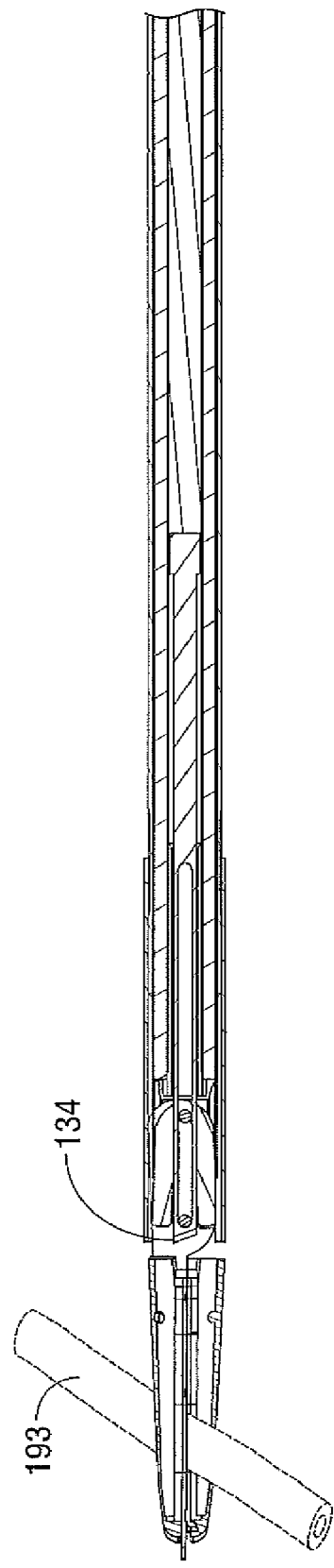

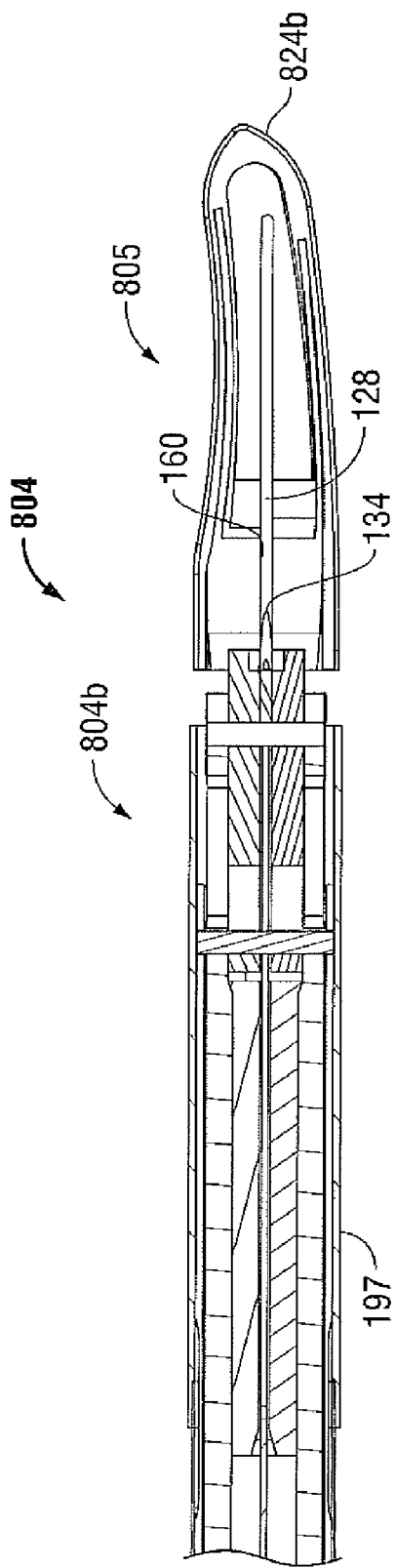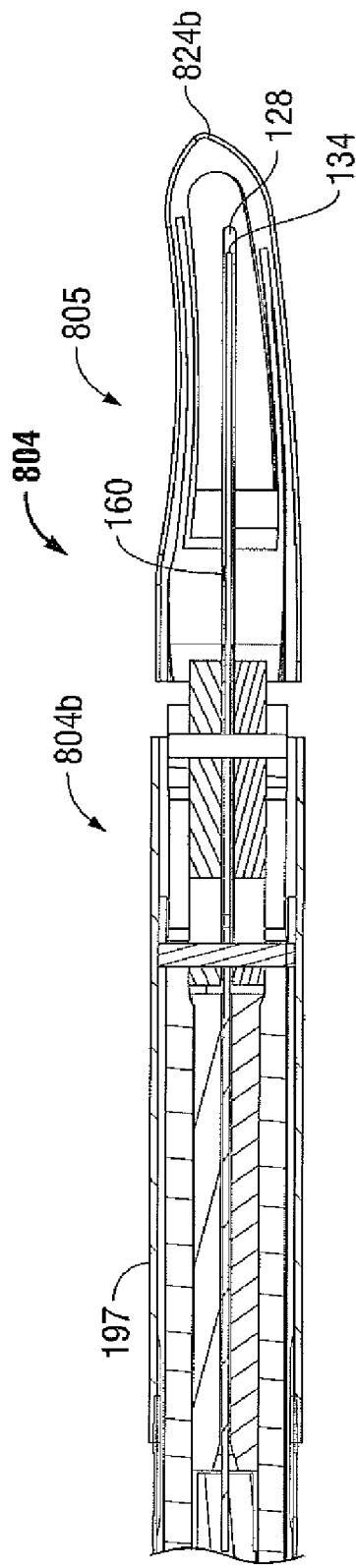
FIG. 11A
FIG. 11B

VESSEL SEALER AND DIVIDER WITH BLADE DEPLOYMENT ALARM

BACKGROUND

1. Technical Field

The present disclosure relates to an apparatus for performing an endoscopic electrosurgical procedure. More particularly, the present disclosure relates to an apparatus for performing an endoscopic electrosurgical procedure that employs an endoscopic electrosurgical apparatus that includes an end effector assembly configured for use with various size access ports.

2. Description of Related Art

Electrosurgical apparatuses (erg., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, fuse, seal, cut, desiccate, and/or fulgurate tissue As an alternative to open electrosurgical forceps for use with open surgical procedures, many modern surgeons use endoscopes and endoscopic electrosurgical apparatus (e.g., endoscopic forceps) for remotely accessing organs through smaller, puncture-like incisions. As a direct result thereof, patients tend to benefit from less scarring, less pain, and reduced healing time. Typically, the endoscopic forceps are inserted into the patient through one or more various types of cannulas or access ports (typically having an opening that ranges from about five millimeters to about fifteen millimeters) that has been made with a trocar; as can be appreciated, smaller cannulas are usually preferred.

Endoscopic forceps that are configured for use with small cannulas (e.g., cannulas less than five millimeters) may present design challenges for a manufacturer of endoscopic instruments.

SUMMARY

Accordingly, the present disclosure is directed to forceps having a pair of jaw members selectively positionable relative to one another about a pivot. Each of the jaw members includes an electrically conductive tissue engaging surface adapted to connect to an electrosurgical energy source. The forceps includes a cutting blade configured to selectively translate within a blade channel defined within at least one of the jaw members. An alarm is operatively coupled to the cutting blade and configured to emit a signal when the cutting blade is deployed into the blade channel. The emission of the signal is independent of the activation of the electrosurgical energy source.

In one embodiment, the forceps includes an alarm configured to emit a signal when the cutting blade is deployed to a predetermined position relative to the blade channel. The forceps may include an alarm that is disposed within at least one of the jaw members and that is configured to emit a signal when the cutting blade moves relative to the blade channel.

In another embodiment, an electrical contact is disposed within the blade channel. The alarm is configured to emit a signal when the cutting blade moves relative to the blade channel and contacts the electrical contact. The forceps may further include a trigger operatively associated with a housing and configured to actuate the cutting blade. The electrical contact may be disposed in the housing. The alarm is configured to emit a signal when the actuator moves relative to the housing and contacts the electrical contact.

In yet another embodiment, the forceps includes an actuator that is operably coupled to the alarm and is configured to emit the signal when the actuator is moved relative to a housing to deploy the cutting blade.

In still another embodiment, an alarm includes one or more resistors that are configured to short and emit the signal upon a predetermined operating condition of the forceps, e.g., deploying the cutting blade, activating the electrosurgical energy, and fully extending the cutting blade. A series of resistors may be arranged in a circuit, the shorting of each resistor of the series indicative of a predetermined operating condition of the forceps. The alarm may be configured to emit a different signal depending upon which predetermined operating condition is satisfied. One or more pressure sensors may be utilized and configured to emit a signal when the cutting blade contacts tissue.

In one embodiment, the alarm includes an optical measurement feature configured to emit a signal upon a predetermined operating condition of the forceps, e.g., deploying the cutting blade, partially extending the cutting blade, fully extending the cutting blade, activating the trigger, partially translating the trigger, fully translating the trigger. The optical measurement feature may be an LED device or an image processing device.

In another embodiment, the alarm includes at least one magnetic sensor configured to emit a signal upon a predetermined operating condition of the forceps. The predetermined operating condition of the forceps includes at least one of cutting blade deployment, cutting blade partially extended, and cutting blade fully extended.

In another aspect, the present disclosure is directed to a method of operating a forceps comprising the first step of: providing a forceps comprising: a pair of jaw members selectively positionable relative to one another about a pivot, each of the jaw members including an electrically conductive tissue engaging surface adapted to connect to an electrosurgical energy source; a cutting blade configured to selectively translate within a blade channel defined within at least one jaw member; and an alarm operatively coupled to the cutting blade and configured to emit a signal when the cutting blade is deployed into the blade channel, wherein the emission of the signal is independent of the activation of the electrosurgical energy source. The method of operating a forceps further comprises the steps of: actuating the forceps to engage tissue; advancing the cutting blade to a predetermined position relative to the blade channel of the forceps; and causing the alarm to emit a signal.

BRIEF DESCRIPTION OF THE DRAWINGS

The above and other aspects, features, and advantages of the present disclosure will become more apparent in light of the following detailed description when taken in conjunction with the accompanying drawings in which:

FIG. 5A is a side cross-sectional view of a distal portion of one embodiment of an electrosurgical forceps engaging tissue in an open configuration;

FIG. 5B is a side cross-sectional view of the distal portion of the electrosurgical forceps of FIG. 5A engaging tissue in a closed configuration;

FIG. 11A is a top plan view of a distal portion of one embodiment of an electrosurgical forceps, an end effector thereof having a first jaw member removed for clarity and a second jaw member including a magnetic sensor; and FIG. 11B is a top plan view of the distal portion of the electrosurgical forceps of FIG. 11A delineating a cutting blade translated into a blade channel of a second jaw member thereof.

DETAILED DESCRIPTION

Figure 1:
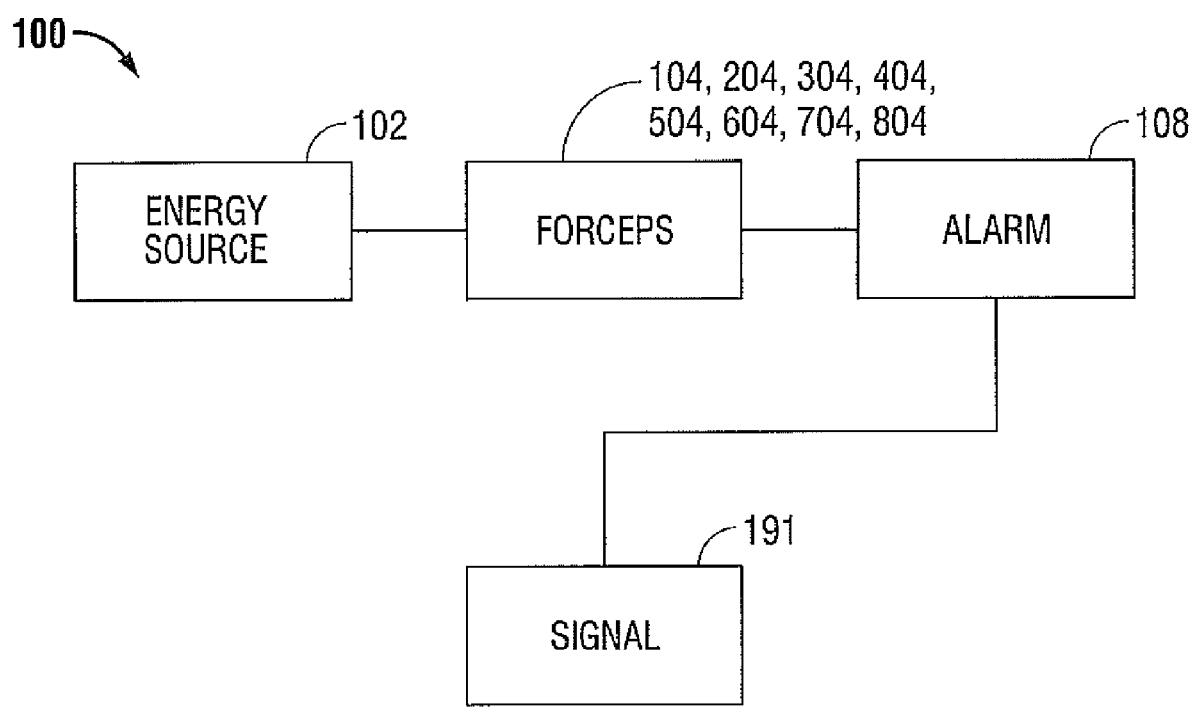
FIG. 1 is a block diagram of an electrosurgical forceps alarm system.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

The present disclosure contemplates an alarm for use in connection with endoscopic, laparoscopic, and open surgical procedures in which the same or similar operating components and features are as described below.

Turning now to FIG. 1, an electrosurgical forceps alarm system 100 is shown for use with various surgical procedures and generally includes an energy source 102 (e.g., an electrosurgical generator), an electrosurgical forceps 104, 204, 304, 404, 504, 604, 704, 804, and an alarm 108 operably associated with the forceps 104, 204, 304, 404, 504, 604, 704, 804 that is configured to emit a signal 191. The energy source 102, the forceps 104, 204, 304, 404, 504, 604, 704, 804, and the alarm 108 mutually cooperate to grasp, seal, and divide tubular vessels and vascular tissue or avascular tissue.

Figure 2A:
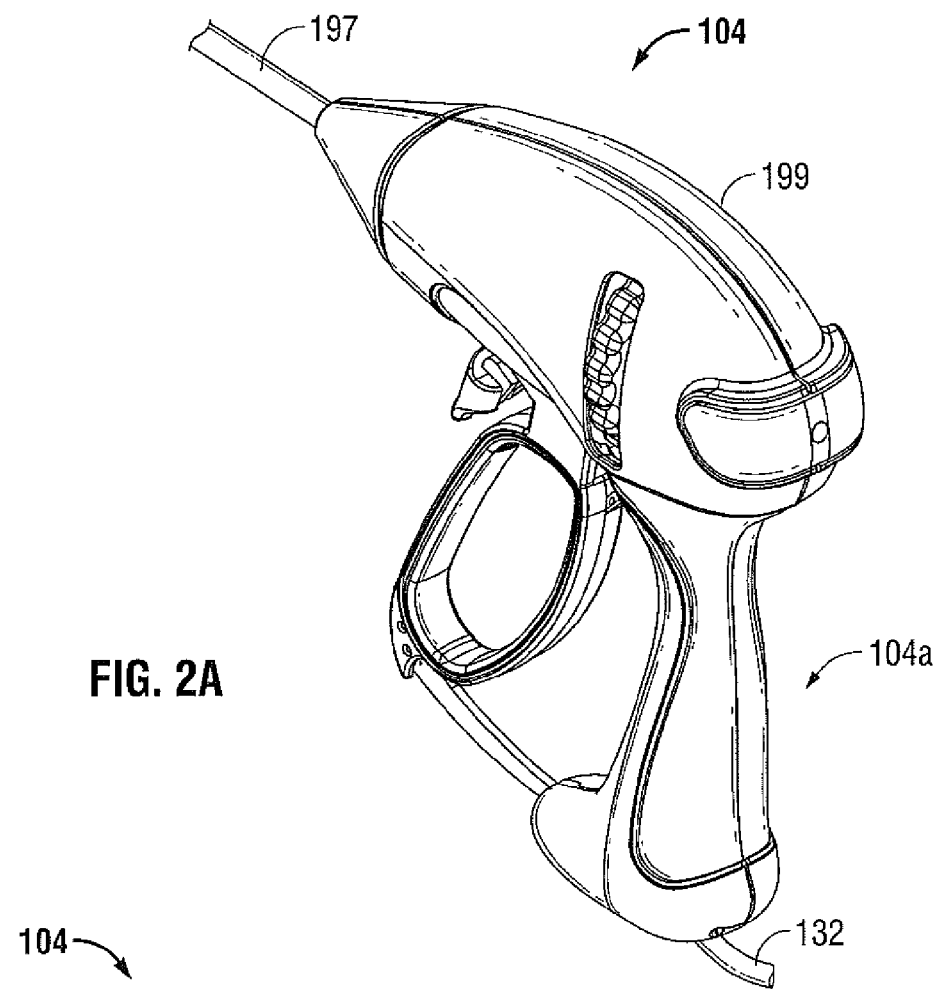
FIG. 2A is a rear perspective view of a proximal portion of an electrosurgical forceps.
Figure 2B:
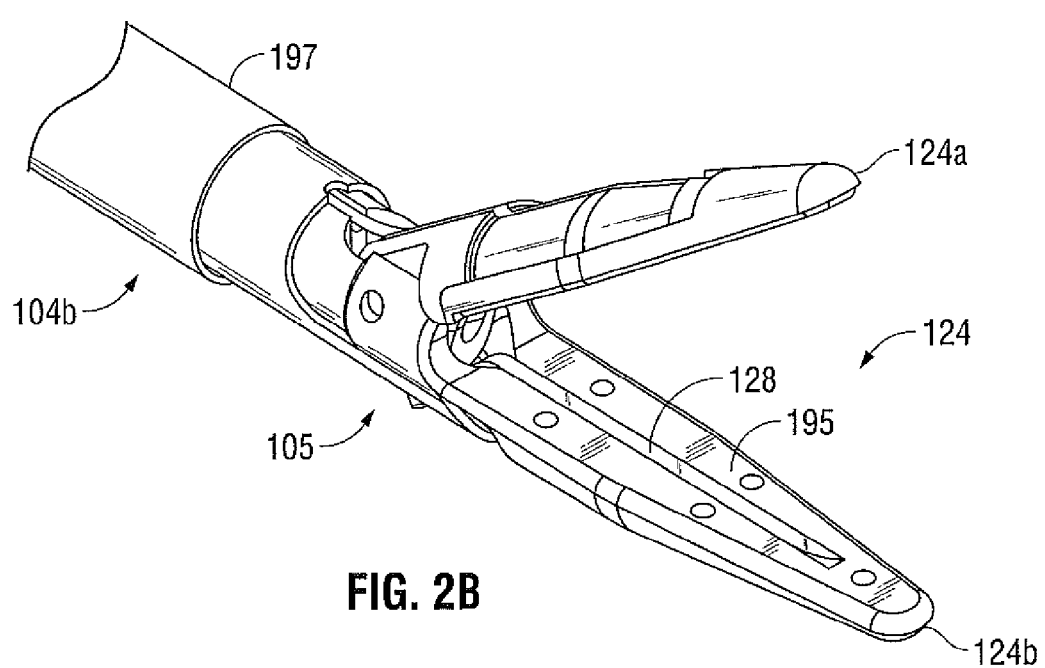
FIG. 2B is a front perspective view of a distal portion of another embodiment of an electrosurgical forceps.

FIGS. 2A and 2B show one embodiment of a forceps 104. The forceps 104 includes an end effector 105 (FIG. 2B) having a pair of jaw members 124 comprising an upper jaw member 124a and a lower jaw member 124b. The end effector is coupled to a shaft 197 of the forceps 104 on the distal portion 104b thereof. Each jaw member 124a, 124b has a blade channel 128 for translation of a cutting blade 134 (not shown) through at least one of the jaw members 124a, 124b during a tissue or vessel cutting procedure. Furthermore, the forceps 104 has an electrosurgical cable 132 coupled to the proximal end 104a thereof for delivering electrosurgical energy to the tissue or vessel when performing a vessel or tissue sealing procedure.

Referring additionally to FIGS. 2A and 2B, forceps 104 includes a housing 199 and a shaft 197 attached thereto. In this embodiment, the forceps 104 has a shaft 197 including a pair of jaw members 124a, 124b disposed at a distal end thereof. The upper and lower jaw members 124a, 124b are operatively coupled to a distal end of the shaft 197 and selectively positionable relative to one another about a pivot, each of the jaw members 124a, 124b having an electrically conductive tissue engaging surface 195 adapted to connect to the energy source 102 (FIG. 1).

Figure 3A:
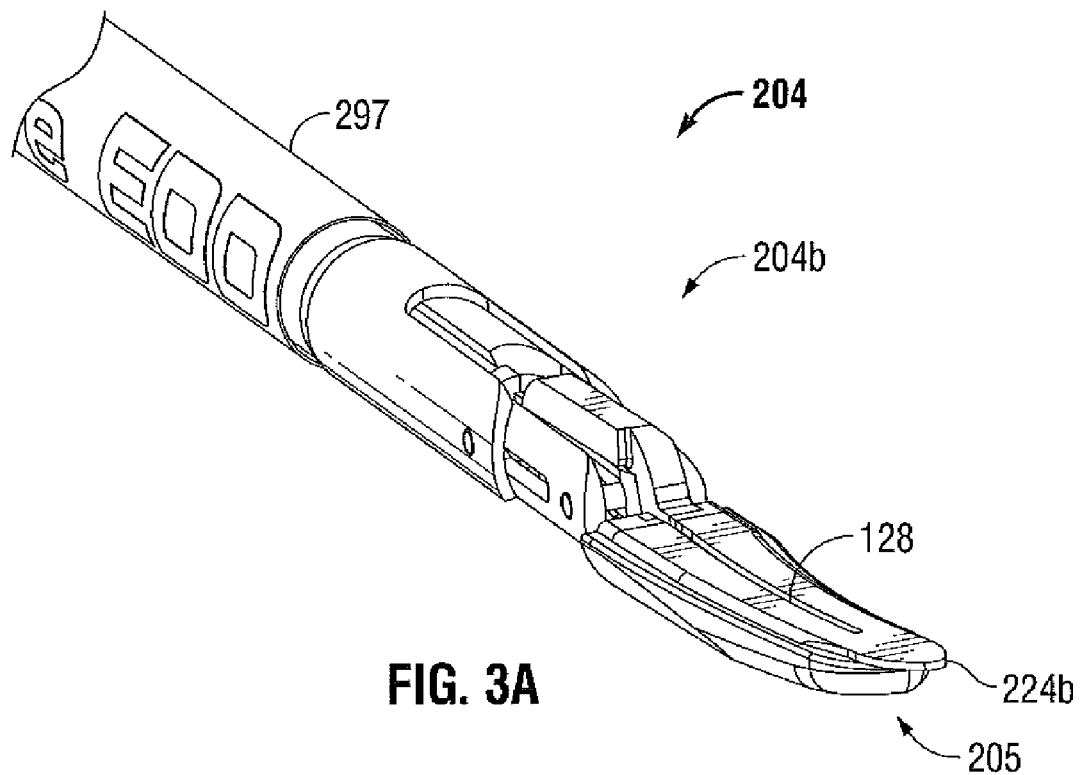
FIG. 3A is a front perspective view of a distal portion of another embodiment of an electrosurgical forceps, an end effector thereof having a first jaw member removed for clarity.
Figure 3B:
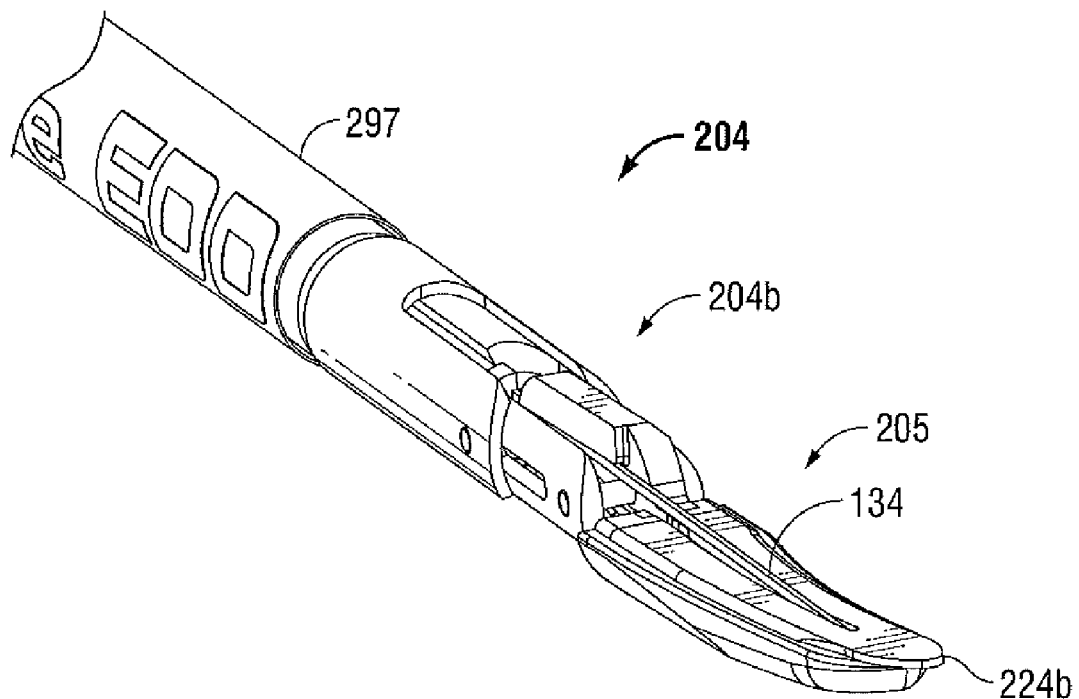
FIG. 3B is a front perspective view of a distal portion of the electrosurgical forceps of FIG. 3A delineating a cutting blade translated into a blade channel of a second jaw member thereof.

Referring to FIGS. 3A and 3B, another embodiment of a distal portion 204b of a forceps 204 includes a cutting blade 134 configured to selectively translate within a blade channel 128 defined within at least one of the jaw members 224a, 224b of the end effector 205. The jaw members 224a, 224b are attached at the distal end of the shaft 297. FIG. 3B shows a cutting blade 134 fully deployed through the blade channel 128 of the lower jaw member 224b of the end effector 205.

Figure 4A:
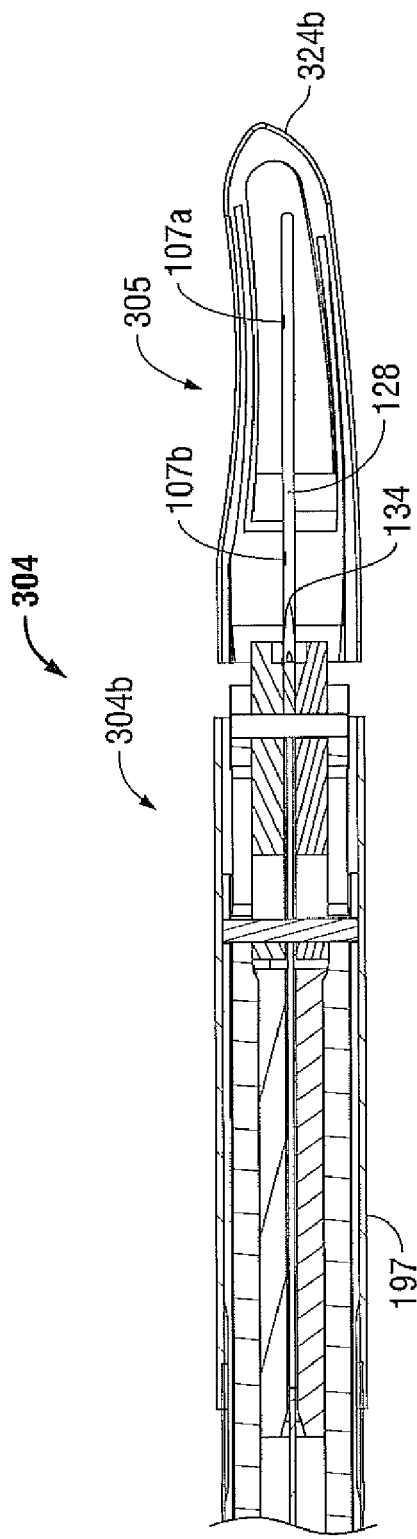
FIG. 4A is a top plan view of a distal portion of yet another embodiment of an electrosurgical forceps, an end effector thereof having a first jaw member removed for clarity and a second jaw member including electrical contacts.
Figure 4B:
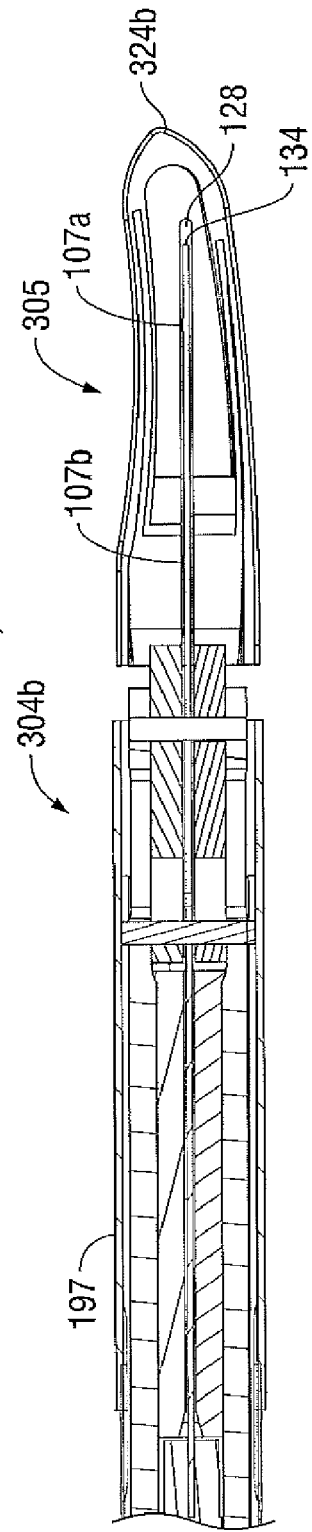
FIG. 4B is a top plan view of the distal portion of the electrosurgical forceps of FIG. 4A delineating a cutting blade translated into a blade channel of a second jaw member thereof.

The alarm 108 (FIG. 1) has contacts 107a, 107b disposed in the blade channel 128 of the end effector 305 (FIGS. 4A and 4B) of yet another embodiment of the distal portion 304b of a forceps 304. As illustrated, the alarm 108 is operatively coupled to the cutting blade 134 and configured to emit a signal 191 when the cutting blade 134 is deployed into the blade channel 128 of the jaw members 324a (not shown), 324b of the end effector 305 or when the cutting blade 134 moves relative thereto. Similarly, the alarm 108 can be configured to emit a signal 191 when the cutting blade 134 moves to a predetermined position relative to the blade channel 128. For example, the alarm 108 can be configured to emit a signal 191 when the cutting blade 134 moves relative to the blade channel 128 and engages contacts 107a, 107b. The emission of the signal 191 can be independent of the activation of the energy source 102.

In operation of one embodiment of the disclosure, when a surgeon deploys the cutting blade 134 and fails to activate electrosurgical energy to the vessel 193 (FIGS. 5A and 5B), the cutting blade 134 will deploy to a predetermined location and set off the alarm 108 which will emit a signal 191, warning the surgeon that the cutting blade 134 has been activated independent of the electrosurgical energy.

Figure 6A:
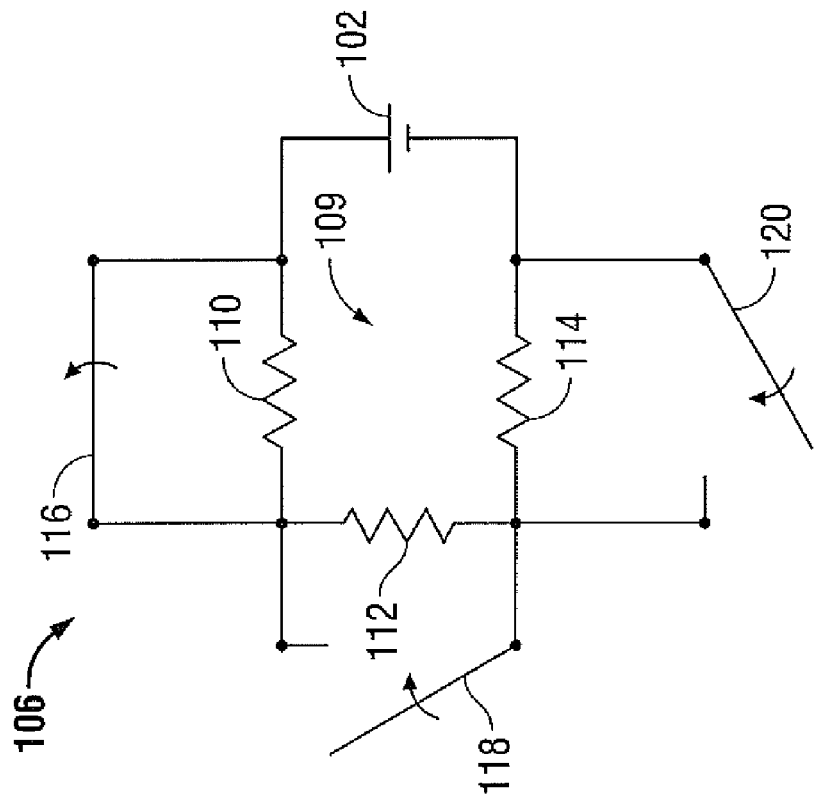
FIG. 6A is a schematic view of a first configuration of an alarm circuit, three of the switches thereof shown in an open configuration.
Figure 6B:
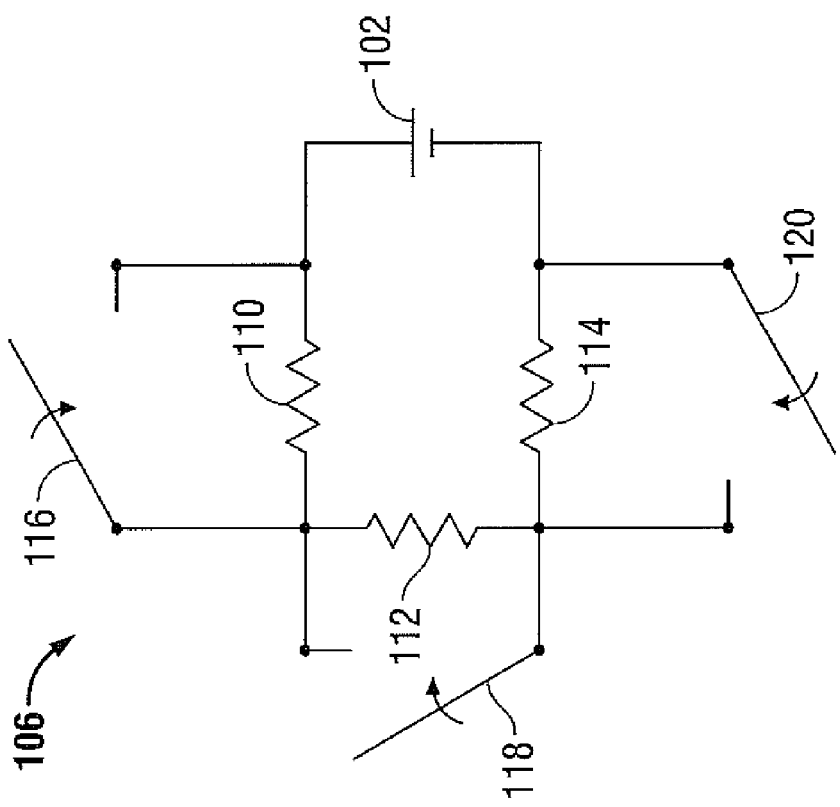
FIG. 6B is a schematic view of a second configuration of the alarm circuit of FIG. 6A, the first switch shown in a closed configuration.

The alarm 108 (FIG. 1) can include an alarm circuit 106 having a first resistance 110, a second resistance 112, and a third resistance 114 coupled to an energy source 102 (FIGS. 6A-6B). The alarm circuit 106 can include one or more resistors 110, 112, 114 that are configured to short and emit a signal 191 upon satisfaction of one or more predetermined operating conditions of the forceps. The predetermined operating conditions of the forceps may include one or more of the following: the deployment of the cutting blade 134, the activation of the electrosurgical energy, and the full extension of the cutting blade 134.

In operation of one embodiment of the disclosure, the cutting blade 134 may deploy as one of the predetermined operating conditions of the forceps. Other predetermined operating conditions include the activation of the electrosurgical energy and the full extension of the cutting blade 134. One or more resistors 110, 112, 114 of the alarm circuit 106 may short, thereby causing the alarm 108 to emit a warning signal 191. The emission of the signal 191 can be independent of the activation of the energy source 102 (FIG. 1).

As illustrated in FIG. 6B, a series of resistances 109 including resistors 110, 112, 114 are arranged in the alarm circuit 106. The shorting of one or more resistors 110, 112, 114 of the series of resistances 109 is indicative of a predetermined operating condition of the forceps. A first switch 116, second switch 118, or third switch 120 may be activated to short a respective first resistance 110, second resistance 112, or third resistance 114. Alternatively, anyone of first, second, or third switch 116, 118, 120 may be arranged to short a plurality of first, second, or third resistors 110, 112, 114. As one skilled in the art can appreciate, these and many other configurations are plausible.

The alarm 108 may be arranged to emit a different signal 191 depending upon which predetermined operating condition is satisfied. The present disclosure also contemplates the emission of different percipient signals 191 including through audition, vision, and tactition. For example, the signal 191 may be a sound, a light, or a vibration. Resistors 110, 112, 114 may readily be interchanged or combined with alternative types of electrical impedance including various arrangements of inductors, capacitors, transistors, etc. Further, various switches 116, 118, 120 may also be used interchangeably, e.g., toggle, pressure, temperature, and the like.

Figure 7:
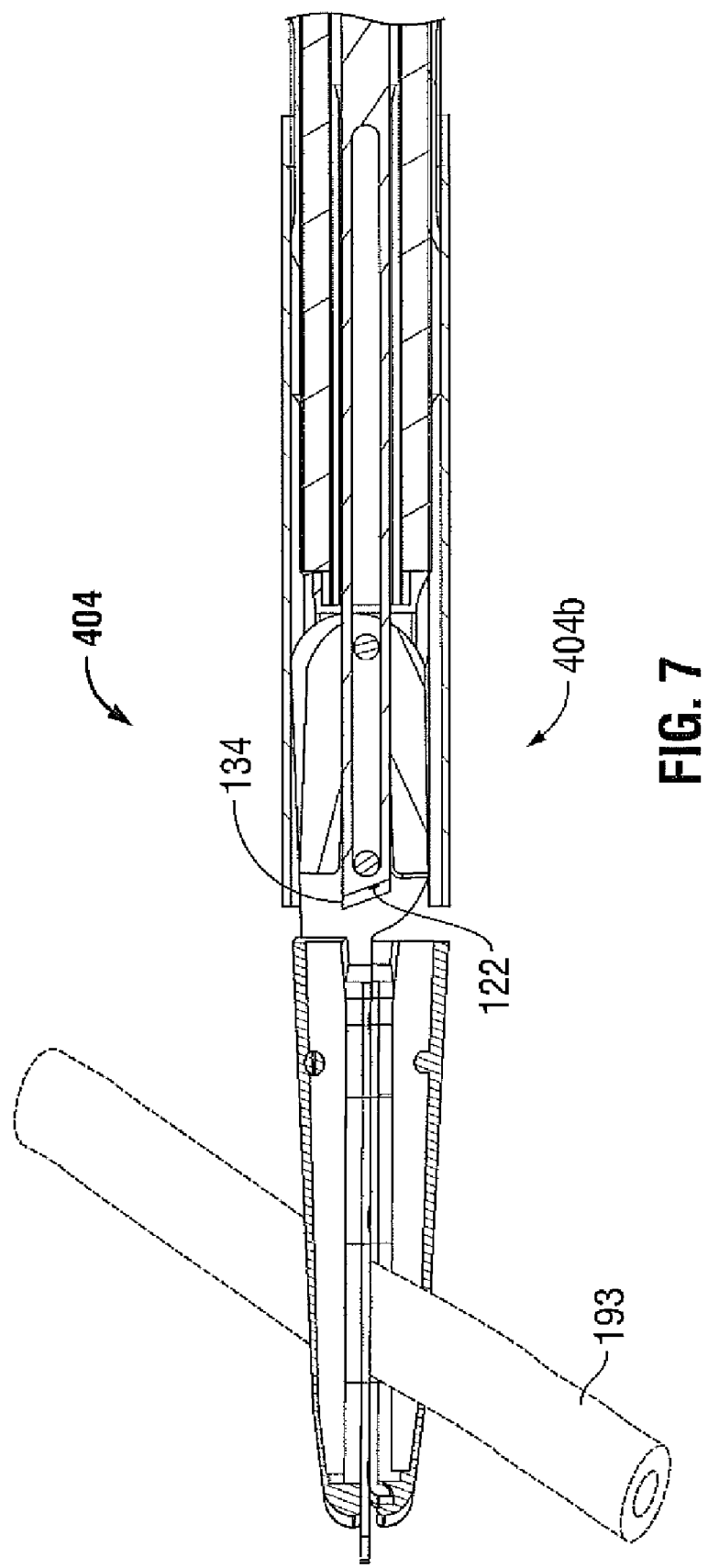
FIG. 7 is an enlarged side cross-sectional view of a distal portion of one embodiment of an electrosurgical forceps, the cutting blade thereof having a pressure sensor.

Referring to FIG. 7, one embodiment of the distal portion 404b of the forceps 404 includes a pressure sensor 122 configured to emit a signal 191 when the cutting blade 134 engages tissue 193. In this embodiment, the pressure sensor 122 is coupled to the distal end of the cutting blade 134. However, the pressure sensor 122 may also be coupled to one or more of the following components of a forceps: the trigger, the handle, the shaft, one or both of the jaw members, or the housing.

Generally, the pressure sensor 122 (FIG. 7) functions in a binary manner. For example, when the cutting blade 134 engages the tissue 193 (FIG. 5A and 5B), pressure is applied to the pressure sensor 122, the pressure sensor 122 then shorts the alarm circuit 106 causing the alarm 108 to emit a warning signal 191. For example, the pressure sensor 122 may operably couple to the handle 136, causing the alarm 108 to emit a warning signal 191 as the handle 136 translates to a predetermined position, wherein the predetermined position can be indicative of a tissue engaging point. The emission of the signal 191 can be independent of the activation of the energy source 102 (FIGS. 1).

Figure 8:
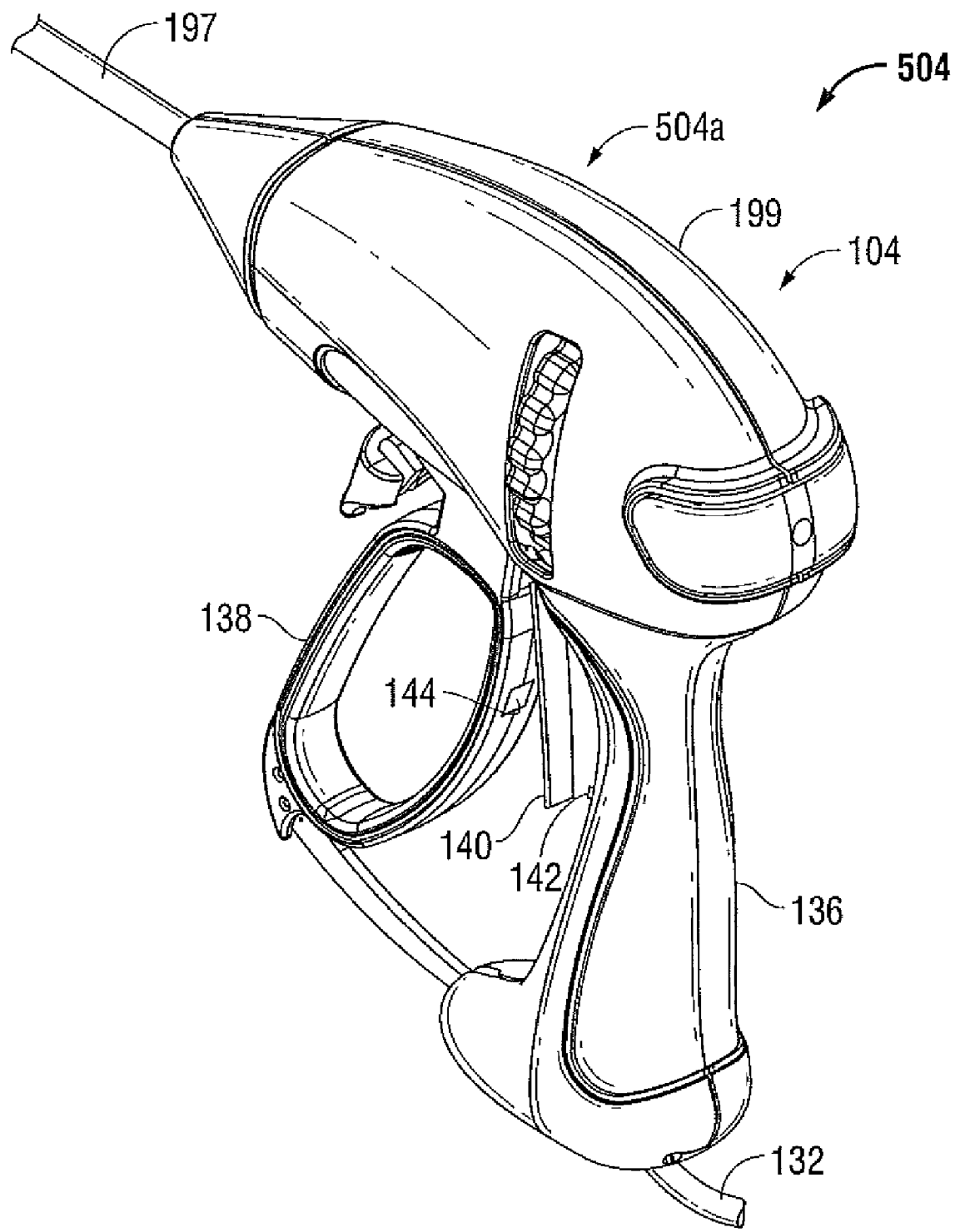
FIG. 8 is a rear perspective view of a proximal portion of another embodiment of an electrosurgical forceps having an electrical contact and contact plates.

Alternatively, a trigger 138 may be operably coupled to the alarm 108, and configured to emit a signal 191 when the trigger 138 is translated, deploying the cutting blade 134 to a predetermined location (FIG. 8).

As illustrated in the embodiment of FIG. 8, the proximal portion 504a of a forceps 504 includes a handle 136 and the trigger 138 is operatively associated with the housing 199 of forceps 104. The forceps 104 has an electrical contact 140 coupled thereto and a first contact plate 142 attached to trigger 138. A second contact plate 144 is attached to the handle 136, wherein each respective contact plate 142, 144 is configured to correspond to a predetermined position of the cutting blade 134. As such, the first and/or second contact plates 142, 144 are arranged to engage the electrical contact 140 to activate the alarm 108 after some translation of the trigger 138.

Other configurations envision having both the first and second contact plates 142, 144 arranged to engage the electrical contact 140 in combination to activate the alarm 108. For example, the trigger 138 enables the alarm 108 to be activated in various configurations when the surgeon translates the trigger 138 to a predetermined position. As such, when the surgeon moves the trigger 138 relative to the housing 199, one or both contact plates 142, 144 contacts the electrical contact 140, causing a short in the alarm circuit 106, which, in turn, causes the alarm 108 to emit a warning signal 191. The emission of the signal 191 can be independent of the activation of the energy source 102 (FIG. 1).

Figure 9:
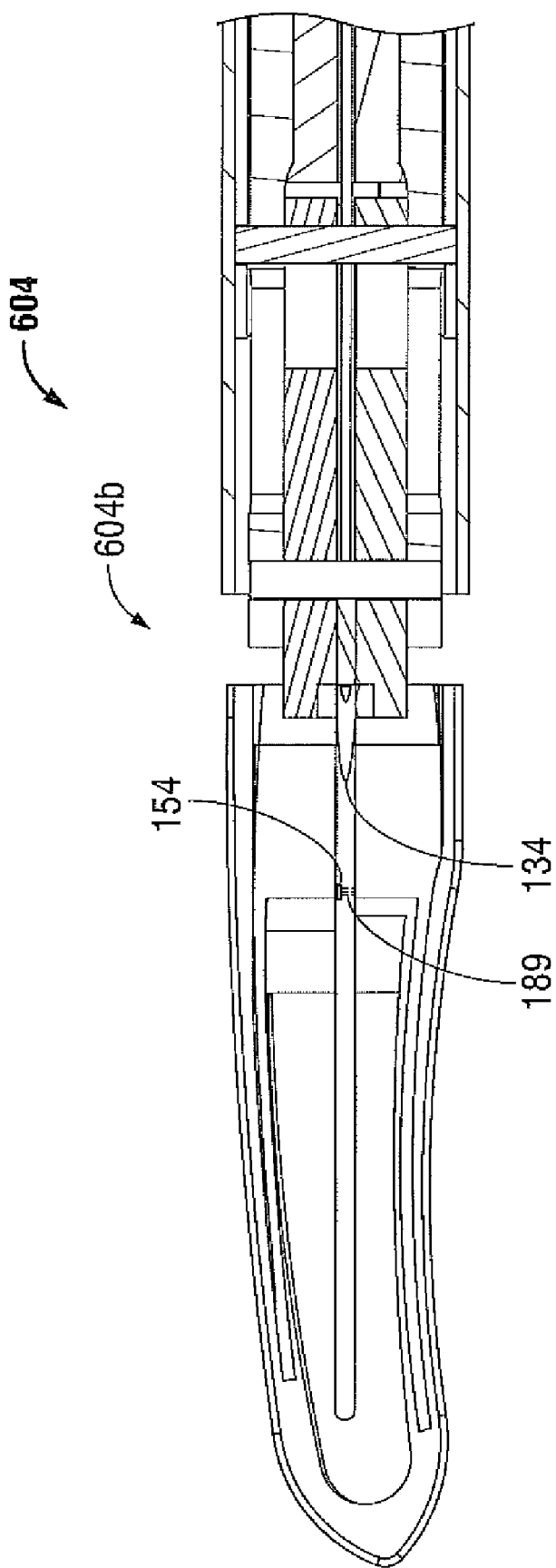
FIG. 9 is an enlarged top plan view of a second jaw member of a further embodiment of the electrosurgical forceps having an optical measurement feature.

Referring to FIG. 9, a further embodiment of the distal portion 604b of a forceps 604 includes an alarm 108 that has an optical measurement feature 154 that is configured to emit a signal 191 upon a predetermined operating condition of the forceps 604. The predetermined operating condition of the forceps 604 may include: cutting blade 134 deployment, cutting blade 134 partially extended, and cutting blade 134 fully extended. FIG. 9 shows an optical measurement feature 154 having an LED (light emitting diode) device. In other configurations, the optical measurement feature 154 includes an image processing device.

A surgeon deploys the cutting blade 134 which translates to a predetermined position. The optical measurement feature 154 detects the position of the cutting blade 134 triggering the alarm 108 to emit a signal 191. For example, the LED projects a beam of light 189 along a bisecting plane transverse to the travel path of the cutting blade 134 at a predetermined location. The cutting blade 134 is deployed and subsequently interferes with the path of the light beam 189, triggering the LED device 154 to short one or more resistances 110, 112, 114 of the alarm circuit 106, causing the alarm 108 to emit a warning signal 191. The emission of the signal 191 can be independent of the activation of the energy source 102 (FIG. 1).

Figure 10:
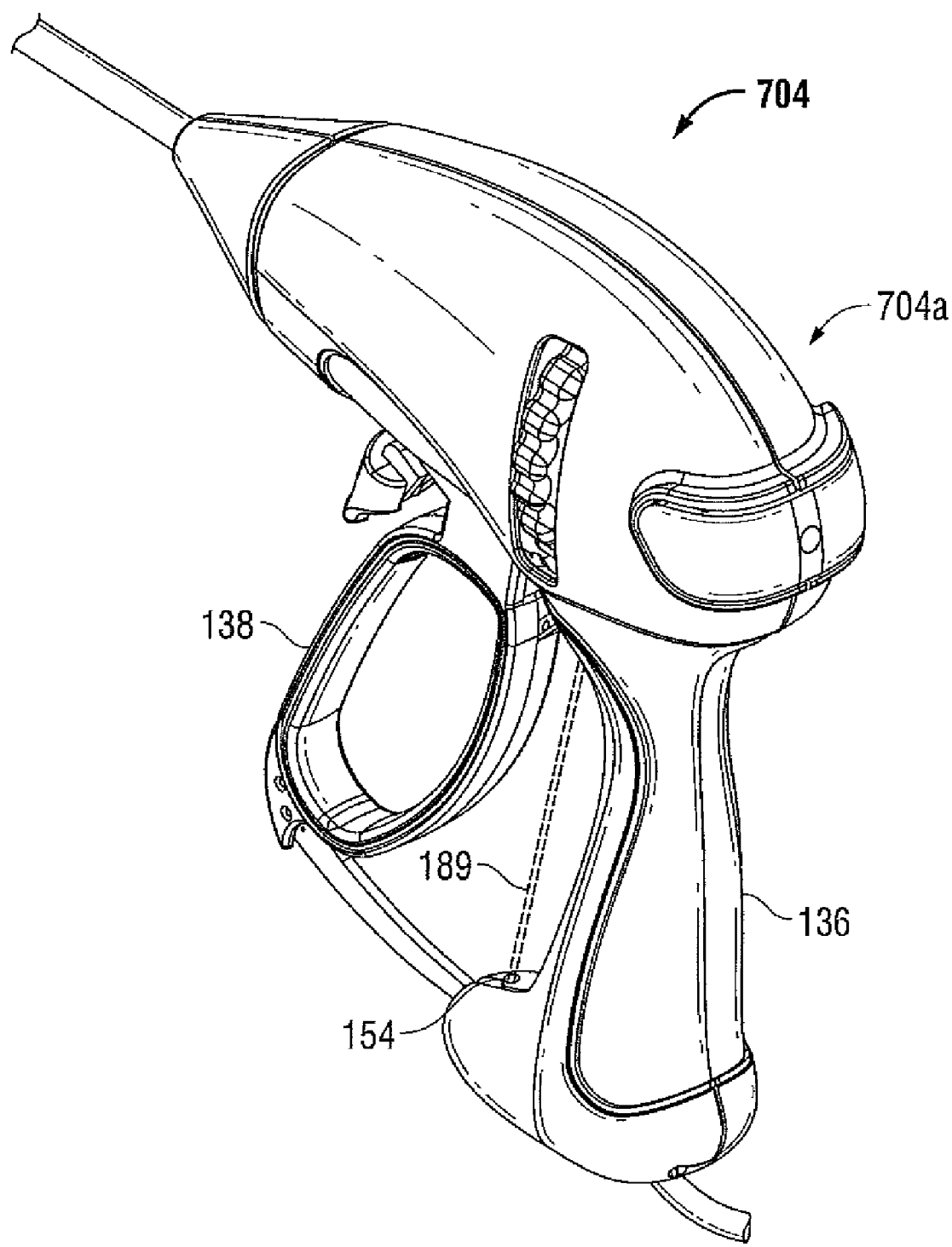
FIG. 10 is a rear perspective view of a proximal portion of another embodiment of an electrosurgical forceps having an optical measurement feature.

Referring to FIG. 10, one embodiment of the of the proximal portion 704a of a forceps 704 includes an optical measurement feature 154 disposed on the handle 136 that is configured to emit a signal 191 upon satisfaction of a predetermined operating condition of the forceps 704 such as trigger 138 activation, trigger 138 partially translated, and trigger 138 fully translated. In certain configurations, the optical measurement feature 154 can be an LED device. In other arrangements, the optical measurement feature 154 may be an image processing device.

In operation of one embodiment of the present disclosure, a surgeon activates the trigger 138. The trigger 138 is translated to a predetermined position and the optical measurement feature 154 detects the position of the trigger 138. This triggers the alarm 108 to emit a signal 191. For example, in an LED arrangement, a beam of light 189 projects along a bisecting plane transverse to the travel path of the trigger 138 at a predetermined location. The trigger 138 interferes with the path of the light beam 189, triggering the LED device 154 to short one or more resistances 110, 112, 114 of the alarm circuit 106, causing the alarm 108 to emit a warning signal 191. The emission of the signal 191 can be independent of the activation of the energy source 102 (FIG. 1).

Referring to FIGS. 11a and 11b, one embodiment of the of the proximal portion 804a of a forceps 804 has an magnetic sensor 160 (e.g., a Hall Effect sensor), that is configured to emit a signal 191 upon a predetermined operating condition of the forceps 804. As illustrated, the alarm 108 (FIG. 1) is operatively coupled to the cutting blade 134 and configured to emit a signal 191 when the cutting blade 134 is deployed into the blade channel 128 of the jaw members 824a (not shown), 824b of the end effector 805 or when the cutting blade 134 moves relative thereto. Similarly, the alarm 108 may be configured to emit a signal 191 when the cutting blade 134 moves to a predetermined position relative to the blade channel 128. For example, the alarm 108 may be configured to emit a signal 191 when the cutting blade 134 moves relative to the blade channel 128 and crosses a magnetic field defined by the magnetic sensor 160 for detecting motion of the cutting blade 134. The emission of the signal 191 may be independent of the activation of the energy source 102 (FIG. 1).

In operation of one embodiment of the disclosure, when a surgeon deploys the cutting blade 134 and fails to activate electrosurgical energy to the vessel 193, the cutting blade 134 will deploy to a predetermined location and trigger the magnetic sensors 160 to cause the alarm 108 to emit a signal 191, warning the surgeon that the cutting blade 134 has been activated independent of the electrosurgical energy. The emission of the signal 191 may be independent of the activation of the energy source 102 (FIG. 1).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A forceps, comprising:
   a housing;
   a trigger movable along a travel path relative to the housing between an untranslated position and a translated position;
   a pair of jaw members selectively positionable relative to one another about a pivot, each of the jaw members including an electrically conductive tissue engaging surface adapted to connect to an electrosurgical energy source;
   a cutting blade configured to selectively translate within a blade channel defined within at least one jaw member in response to movement of the trigger; and
   an alarm including at least a portion extending along a plane into the travel path of the trigger, the alarm emitting a signal when the trigger crosses the plane as the trigger moves between the untranslated position and the translated position, the signal indicative of the cutting blade being deployed into the blade channel, wherein the emission of the signal is independent of the activation of the electrosurgical energy source.

2. A forceps according to claim 1, wherein the alarm is configured to emit the signal when the cutting blade is deployed to a predetermined position relative to the blade channel.

3. A forceps according to claim 1, wherein the alarm is disposed within at least one of the jaw members and emits the signal when the cutting blade moves relative to the blade channel.

4. A forceps according to claim 1, wherein the alarm includes an electrical contact disposed within the blade channel and wherein the alarm is configured to emit the signal when the cutting blade moves relative to the blade channel and contacts the electrical contact.

5. A forceps according to claim 1, wherein the trigger is coupled to the alarm.

6. A forceps according to claim 1, wherein the alarm includes an electrical contact disposed on the housing and wherein the alarm is configured to emit the signal when the trigger moves relative to the housing and contacts the electrical contact.

7. A forceps according to claim 1, wherein the alarm includes at least one resistor which is configured to short and emit the signal upon a predetermined operating condition of the forceps, the predetermined operating condition of the forceps including at least one of cutting blade deployment, activation of electrosurgical energy, and cutting blade fully extended.

8. A forceps according to claim 7, wherein a series of resistors are arranged in a circuit, the shorting of each resistor of the series indicative of a predetermined operating condition of the forceps.

9. A forceps according to claim 7, wherein the alarm is configured to emit a different signal depending upon which predetermined operating condition is satisfied.

10. A forceps according to claim 1, wherein the alarm includes at least one pressure sensor configured to emit the signal when the cutting blade contacts tissue.

11. A forceps according to claim 1, wherein the alarm includes an optical measurement feature configured to emit the signal upon a predetermined operating condition of the forceps, the predetermined operating condition of the forceps including at least one of cutting blade deployment, cutting blade partially extended, and cutting blade fully extended.

12. A forceps according to claim 1, wherein the alarm includes an optical measurement feature configured to emit the signal upon a predetermined operating condition of the forceps, the predetermined operating condition of the forceps including at least one of trigger activation, trigger partially translated, and trigger fully translated.

13. A forceps according to claim 11, wherein the optical measurement feature is an LED device.

14. A forceps according to claim 12, wherein the optical measurement feature is an LED device.

15. A forceps according to claim 11, wherein the optical measurement feature is an image processing device.

16. A forceps according to claim 12, wherein the optical measurement feature is an image processing device.

17. A forceps according to claim 1, wherein the alarm includes at least one magnetic sensor configured to emit the signal upon a predetermined operating condition of the forceps, the predetermined operating condition of the forceps including at least one of cutting blade deployment, cutting blade partially extended, and cutting blade fully extended.

* * * * *